United States Patent
Kodama et al.

(10) Patent No.: US 7,130,680 B2
(45) Date of Patent: Oct. 31, 2006

(54) BODY COMPOSITION MEASUREMENT APPARATUS

(75) Inventors: Miyuki Kodama, Tokyo (JP); Yasuhiro Kasahara, Tokyo (JP)

(73) Assignee: Tanita Corporation, Tokyo (JP)

( * ) Notice: Subject to any disclaimer, the term of this patent is extended or adjusted under 35 U.S.C. 154(b) by 228 days.

(21) Appl. No.: 10/832,404

(22) Filed: Apr. 27, 2004

(65) Prior Publication Data

US 2004/0220492 A1   Nov. 4, 2004

(30) Foreign Application Priority Data

May 2, 2003   (JP)   ............... 2003-127028

(51) Int. Cl.
*A61B 5/05*   (2006.01)
(52) U.S. Cl. ...................... 600/547; 600/554
(58) Field of Classification Search ............... 600/547, 600/554
See application file for complete search history.

(56) References Cited

U.S. PATENT DOCUMENTS

| | | | | |
|---|---|---|---|---|
| 5,372,141 A | * | 12/1994 | Gallup et al. ............... | 600/547 |
| 5,579,782 A | * | 12/1996 | Masuo ........................ | 600/547 |
| 5,720,296 A | * | 2/1998 | Cha ............................ | 600/554 |
| 5,788,643 A | * | 8/1998 | Feldman ..................... | 600/506 |
| 6,256,532 B1 | * | 7/2001 | Cha ............................ | 600/547 |
| 6,327,494 B1 | * | 12/2001 | Sakai .......................... | 600/547 |
| 6,393,317 B1 | * | 5/2002 | Fukuda et al. ............... | 600/547 |
| 6,490,481 B1 | * | 12/2002 | Komatsu et al. ............ | 600/547 |
| 6,516,221 B1 | * | 2/2003 | Hirouchi et al. ............ | 600/547 |
| 2001/0053883 A1 | | 12/2001 | Yoshimura et al. | |
| 2002/0165464 A1 | | 11/2002 | Singer | |
| 2003/0050570 A1 | | 3/2003 | Kodama | |

FOREIGN PATENT DOCUMENTS

| | | |
|---|---|---|
| EP | 1 118 308 A1 | 7/2001 |
| EP | 1 138 259 A2 | 10/2001 |
| EP | 1 279 366 A2 | 1/2003 |
| JP | P3330951 | 7/2001 |
| JP | P2003-24293 | 1/2003 |
| WO | WO 96/19141 | 6/1996 |

\* cited by examiner

*Primary Examiner*—Max F. Hindenburg
*Assistant Examiner*—Rene Towa
(74) *Attorney, Agent, or Firm*—McDermott Will & Emery LLP

(57) ABSTRACT

Disclosed is a body composition measurement apparatus, comprising: a current supplying unit; a voltage measurement unit; a bioelectrical impedance measurement unit; and a judgment unit. According to the present invention said current supplying unit supplies an electric current to a person under test, said voltage measurement unit measures an electric voltage, and said bioelectrical impedance measurement unit measures a parameter for bioelectrical impedance of a measured part of the person, based on the current supplied and the voltage measured. Furthermore, said judgment unit judges an index for cell age of the person, based on the measured parameter for bioelectrical impedance.

18 Claims, 11 Drawing Sheets

| BODY BUILD AGE LEVEL \ CELL AGE LEVEL | REAL AGE LESS THAN −10% | REAL AGE NOT LESS THAN −10% ~ LESS THAN +10% | REAL AGE NOT LESS THAN +10% |
|---|---|---|---|
| REAL AGE LESS THAN −10% | BODY BUILD AGE IS MATCHED TO CELL AGE AND BOTH ARE YOUNGER THAN REAL AGE. IT'S IDEAL. KEEP THIS CONDITION. | BODY BUILD AGE IS YOUNGER THAN REAL AGE, BUT CELL AGE IS STANDARD. YOU MAY HAVE LOWER BODILY POWER THAN APPEARANCE. NO PROBLEM, BUT DON'T OVERESTIMATE YOUR BODILY POWER IRRESPECTIVE OF YOUNG APPEARANCE. | BODY BUILD AGE IS YOUNGER THAN REAL AGE, BUT CELL AGE IS ACTUALLY ADVANCED. TAKE CARE! PAY ATTENTION TO THE GAP BETWEEN THE APPEARANCE AND THE ACTUAL CONDITION. NEVER OVERESTIMATE YOUR BODILY POWER. FREQUENTLY TAKE REST AND SUPPLEMENT WATER UPON DOING EXERCISE. |
| REAL AGE NOT LESS THAN −10% ~ LESS THAN +10% | BODY BUILD HAS STANDARD BALANCE FOR REAL AGE, BUT CELL AGE IS YOUNGER THAN REAL AGE. NO PROBLEM. YOU HAVE BODILY POWER, SO YOU MAY HAVE YOUNGER BODY BUILD IF YOUR ARMS AND ABDOMEN BECOME TIGHT. | TYPICAL TYPE IN WHICH THERE IS MATCH BETWEEN REAL AGE, BODY BUILD AGE AND CELL AGE. NO PROBLEM. BUT, BE WATCHFUL! BODY BUILD AGE AND CELL AGE WOULD RAPIDLY BE ADVANCED IF YOU HAVE AN IDLE LIFE. | BODY BUILD HAS STANDARD BALANCE FOR REAL AGE, BUT CELL AGE IS ACTUALLY ADVANCED. AGE IS MORE ADVANCED THAN APPEARANCE. NEVER OVERESTIMATE YOUR BODILY POWER. FREQUENTLY TAKE REST AND SUPPLEMENT WATER DOING EXERCISE. |
| REAL AGE NOT LESS THAN +10% | CELL AGE IS YOUNGER THAN REAL AGE, BUT BODY BUILD MAY LOOK OLDER THAN REAL AGE. YOU MAY HAVE YOUNGER BODY BUILD IF YOUR ARMS AND ABDOMEN BECOME TIGHT. DO EXERCISE ACTIVELY! | CELL AGE IS MATCHED TO REAL AGE AND IS STANDARD, BUT BODY BUILD MAY LOOK OLDER THAN REAL AGE. YOU MAY HAVE YOUNGER BODY BUILD IF YOUR ARMS AND ABDOMEN BECOME TIGHT. DO EXERCISE ACTIVELY! | BOTH BODY BUILD AGE AND CELL AGE ARE MORE ADVANCED THAN REAL AGE. YOU MAY HAVE YOUNGER BODY BUILD IF YOUR ARMS AND ABDOMEN BECOME TIGHT. DO EXERCISE ACTIVELY! BUT, SUFFICIENTLY TAKE REST AND SUPPLEMENT WATER IN ORDER NOT TO ACCUMULATE FATIGUE. |

FIG. 13

BODY COMPOSITION MEASUREMENT APPARATUS

BACKGROUND OF THE INVENTION

1. Field of the Invention

The present invention relates to an apparatus for assessing body composition for each of measured parts of a person under test using a bioelectrical impedance analysis ("BIA") method, and more particularly to, an apparatus for totally assessing the body composition by combination of various measurement results.

2. Prior Art

The bioelectrical impedance analysis has generally been conducted in such manner that the measurement of body composition of a person is performed for each of the parts of the person and the measurement result of body composition is numerically displayed or compared to the standard range. An apparatus has been proposed in which what age the visceral fat mass or basal metabolism belongs to is determined as the index of body composition and the result thereof is displayed (Patent Document 1, for example).

Another apparatus has been known in which a bioelectrical impedance analysis is performed to assess the amount of cells of a person. Furthermore, an additional apparatus has also been known in which the amount of body cells, the fat free mass and the total body water of a person are estimated on the basis of measurement of height or body weight and bioelectrical impedance (Patent Document 2, for example).

Patent Documents associated with the present invention are as follows:

Patent Document 1:
Japanese Patent Laid-Open No. 2003/24293
Patent Document 2:
Japanese Patent No. 3330951

The apparatus, as described in Japanese Patent Laid-Open No. 2003/24293, is configured to simply determine what age the visceral fat mass or basal metabolism belongs to as the index of each body composition. The apparatus additionally generates an advice for the person depending on the combination of the visceral fat mass, basal metabolism and "BMI".

In particular, a distribution balance for body composition elements such as fat mass, fat free mass and muscle amount, that is an index greatly depending on change in body build with the age, has not been assessed in association with the age.

Furthermore, Japanese Patent No. 3330951 describes a concrete equation of estimation used only for assessing the amount of cells of the person, but there is no further description found therein.

In view of the above, an object of the present invention is to determine what age the body build of a person under test belongs to. More particularly, the present invention aims at judging any change in cells with the age, that can't externally be seen, for totally assessing the body build of the person in view of the age, for assessing any difference between any change in body build with the age and any change in cells with the age, and for producing an advice message useful for behavior in the life of the person according to the result of assessments.

SUMMARY OF THE INVENTION

In order to attain such object the present invention provides a body composition measurement apparatus, comprising: a current supplying unit; a voltage measurement unit; a bioelectrical impedance measurement unit; and a judgment unit, wherein said current supplying unit supplies an electric current to a person under test, said voltage measurement unit measures an electric voltage, said bioelectrical impedance measurement unit measures a parameter for bioelectrical impedance of a measured part of the person, based on the current supplied and the voltage measured, and said judgment unit judges an index for cell age of the person, based on the measured parameter for bioelectrical impedance, thereby the assessment of body composition of the person in view of the age is performed.

In one embodiment of the present invention size of a cell is used as the index for cell age, thereby the assessment of cell age is performed.

In another embodiment of the present invention cell-retained water is used as the index for cell age, thereby the assessment of cell age is performed.

In further embodiment of the present invention said judgment unit compares the judged index for cell age to the real age of the person for assessing the cell age of the person.

In another aspect the present invention provides a body composition measurement apparatus, comprising: a current supplying unit; a voltage measurement unit; a bioelectrical impedance measurement unit; and a judgment unit, wherein said current supplying unit supplies an electric current to a person under test, said voltage measurement unit measures an electric voltage, said bioelectrical impedance measurement unit measures a parameter for bioelectrical impedance of a measured part of the person, based on the current supplied and the voltage measured, and said judgment unit judges an index for body build age of the person, based on the measured parameter for bioelectrical impedance, thereby the assessment of body build age of the person is performed.

In one embodiment of the present invention said index for body build age has such value that is calculated based on a parameter for main body fat and a parameter for leg fat or muscle, thereby the assessment of body build age of the person is performed.

In another embodiment of the present invention main body fat distribution rate is used as the index for body build age, thereby the assessment of body build age of the person is performed.

In further embodiment of the present invention said judgment unit compares said judged index for body build age to the real age of the person for assessing the body build age of the person.

In further aspect the present invention provides a body composition measurement apparatus, comprising: a current supplying unit; a voltage measurement unit; a bioelectrical impedance measurement unit; and a judgment unit, wherein said current supplying unit supplies an electric current to a person under test, said voltage measurement unit measures an electric voltage, said bioelectrical impedance measurement unit measures a parameter for bioelectrical impedance of a measured part of the person, based on the current supplied and the voltage measured, and said judgment unit includes
an index change judgment portion that judges any change in index for cell and body build of the person with the age, based on the measured parameter for bioelectrical impedance,
a cell assessment portion that compares the judged change in index for cell with the age to the real age of the person for assessing the cell age of the person, and
a body build assessment portion that compares the judged change in index for body build with the age to the real age of the person for assessing the body build age of the person, whereby
the body composition of the person in view of the age is judged, based on the combination of said assessments for the cell age and the body build age of the person.

In one embodiment of the present invention the body composition measurement apparatus further comprises an advice generation unit, said advice generation unit generating an advice message in response to the judged body composition of the person in view of the age.

BRIEF DESCRIPTION OF THE DRAWINGS

Now, the present invention will be described in more detail with reference to the accompanying drawings, in which:

FIG. 12 is a table on the basis of which the body composition measurement apparatus makes assessment and produces an advice message.

DESCRIPTION OF THE PREFERRED EMBODIMENTS

The present inventor measured fat rate (% FAT), fat mass (FATkg) and fat free mass (FFMkg) for a whole body and each part of each of persons under test using a bioelectrical impedance analysis ("BIA") method and then compared the average values for the parts of the persons for each of the ages. As the result, it has been found that for male persons the fat rate "% FAT" for an upper limb (or an arm) and a trunk is increased with the age, but the fat free mass "FFM" for a lower limb (or a leg) is reduced. On the other hand, for female persons, the fat rate "% FAT" and the fat mass for all the parts are increased. In particular, those for a trunk and an upper limb are greatly increased.

Upon considering any change in fat rate for each part at each of the ages the male persons have substantially uniform fat rate for all the parts except for the arms when they are young, but they tend to have higher fat rate for trunks than for other parts as they reach the old and middle age. On the other hand, the female persons have so-called "lower-half body" type fat distribution exhibiting that the fat rate for lower limbs have the highest values when they are young, but the fat rate for the trunk and each of parts is increased with the age so that there becomes no difference in fat rate between the parts.

As the overall result, both male and female persons tend to increase in fat rate for upper-half body, but to decrease in fat free mass for lower limbs with the age. In particular, the fat distribution for female person is significantly changed, with the age, from "higher in lower-half body" condition to "adiposity in upper-half body" condition that resembles the body build of the male person. That is to say, it has been found that the body composition is not uniformly changed over a whole body with the age, but differently changed with male and female persons for different parts thereof.

Accordingly, an apparatus of the present invention is configured to determine youngness of a person under test in view of his/her body build by indicating what age the body build of the person belongs to, depending on the standard distribution of fat mass, fat free mass and muscle for each of the ages, using the value resulting from assessment for body composition due to "BIA" for each of the parts of the person. Furthermore, some value that is deeply related to any change in cells with the age, such as the ratio of intracellular and extracellular waters, cell size ("BCM": Body Cell Mass), reactance, phase angle, etc. is estimated by "BIA" method using multiple frequencies, and then, it is compared to the average value thereof in order to determine the youngness at cell level, which is never seen from the outside of the body. With combination of those results an overall determination of age by taking into account of any change in body build element with the age, such as distribution of fat or muscle, and any change in quality of cells with the age is performed, together with a determination of any difference between both changes. Then, the result of such determination is displayed on the apparatus, along with an advice message useful for behavior in the life according to the result.

In particular, it is suggested that there is intimate relation between main body fat and dangerous factor for lifestyle related disease. Therefore, any suitable decision and advice, if provided, assists for prevention of lifestyle related disease.

Figure 1:
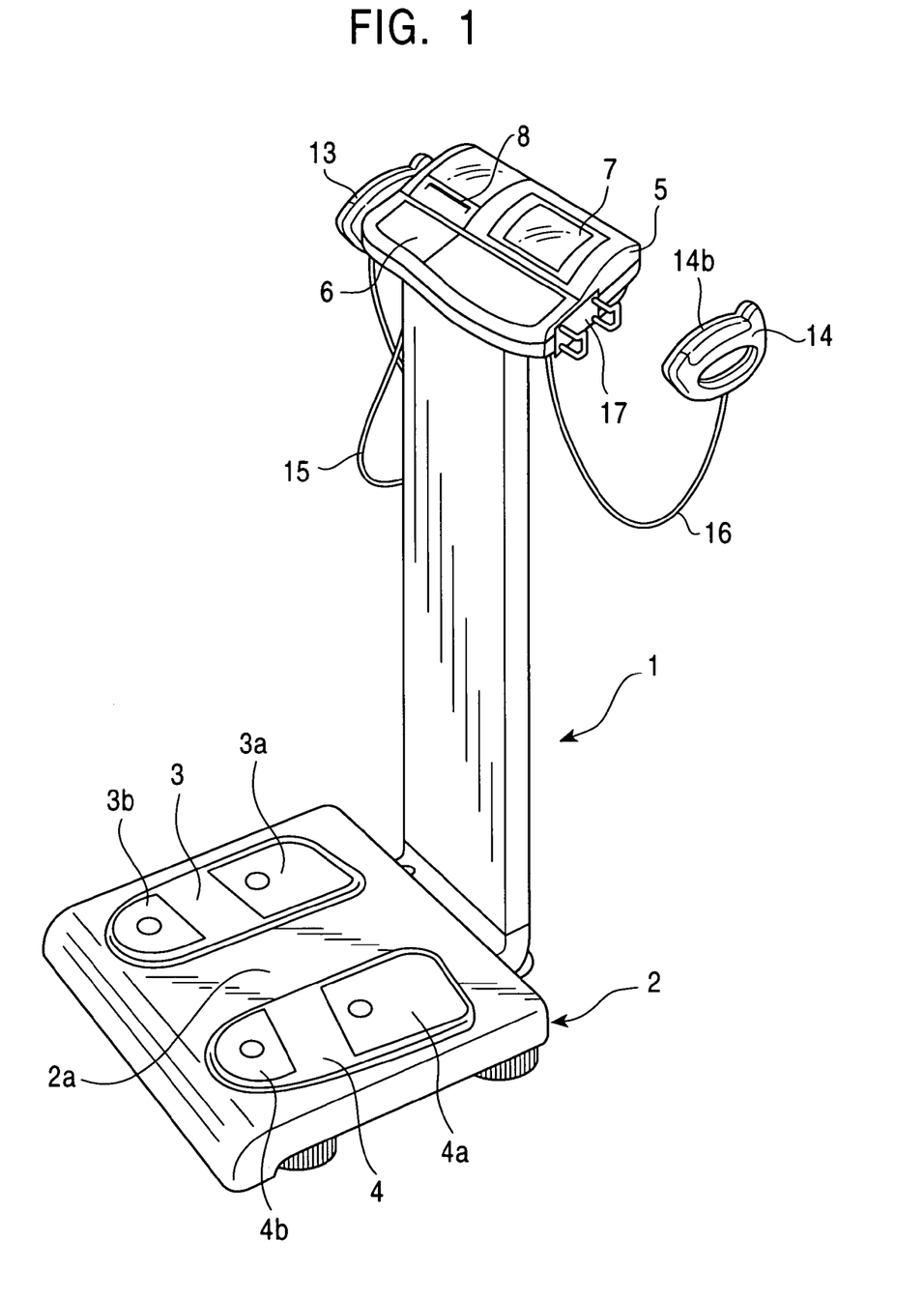
FIG. 1 is an external view of a body composition measurement apparatus according to one embodiment of the present invention.
Figure 2:
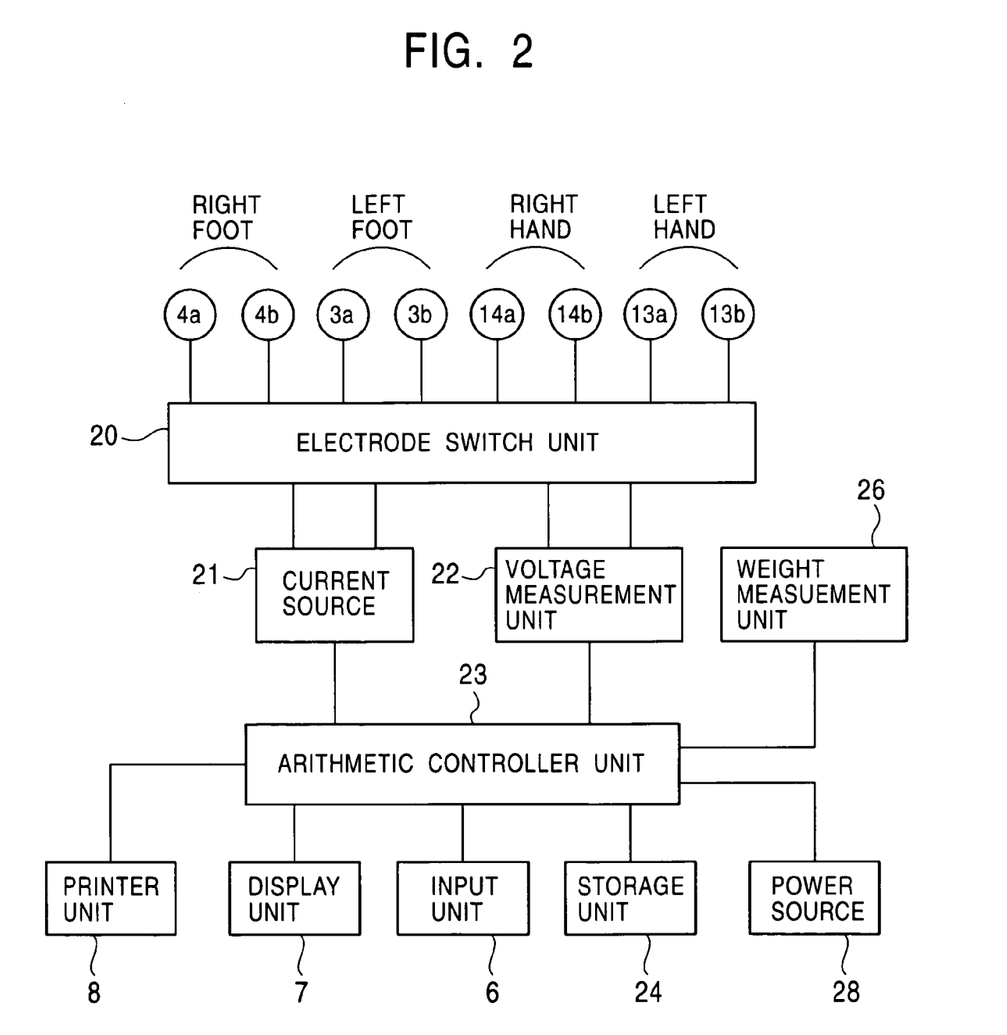
FIG. 2 is an internal block diagram of the body composition measurement apparatus.

FIG. 1 is an external view of a body composition measurement apparatus according to an embodiment of the present invention; and FIG. 2 is an electrical block diagram for the apparatus.

Referring to FIG. 1, the body composition measurement apparatus 1 has a generally "L" shaped configuration. A weight meter 2 having prior art construction is provided on a lower portion of the measurement apparatus. The weight meter 2 includes a platform 2a on which a person under test mounts for measuring the body weight. Foot electrodes 3, 4 are provided on the platform 2a for contacting with soles of left and right feet of the person who mounts on the platform. In particular, the electrodes 3, 4 consist of current supplying electrodes 3a, 4a and voltage measurement electrodes 3b, 4b.

An operation box 5 is provided on top of the measurement apparatus 1. The operation box 5 includes an input unit 6 having a plurality of keys such as a power switch and numerical keys provided therein for entering each type of body information, a display unit 7 or a dot-matrix LCD for displaying measurement result, and a printer unit 8 for printing measurement result on a paper which is then discharged.

In addition, the operation box 5 is connected to hand electrode grips 13, 14 via cords 15, 16. The hand electrode grips 13, 14 also consist of current supplying electrodes 13a, 14a and voltage measurement electrodes 13b, 14b. The hand electrode grips 13, 14 are set on hooks 17 on both left and right sides of the operation box 5 at the time except for measurement being done.

FIG. 2 is an internal electrical block diagram of the measurement apparatus 1. Eight electrodes 3a, 3b, 4a, 4b, 13a, 13b, 14a, 14b that are contact with left and right feet and hands for current supplying and voltage measurement are connected to an electrode switch unit 20. The electrode switch unit 20 is then connected to an arithmetic controller unit 23 via a current source 21 and a voltage measurement unit 22. The arithmetic controller unit 23 includes a microcomputer (CPU) which acts as a bioelectrical impedance calculation means for calculating the bioelectrical impedance based on the current supplied and the voltage measured and as a correction means for correcting the bioelectrical impedance calculated. It also acts as a body composition calculation means for calculating an index for living body composition, in addition to other arithmetic operation and control. Also connected to the arithmetic controller unit 23 are a storage unit 24 consisting of a memory or a register for storing each type of data and a weight measurement unit 26 for measuring body weight of a person under test. Furthermore, the input unit 6, the display unit 7 and the printer unit 8 are connected to the arithmetic controller unit 23. A power source 28 supplies power to the arithmetic controller unit 23 and other units.

Now, operation of the body composition measurement apparatus will be described in more detail.

Figure 3:
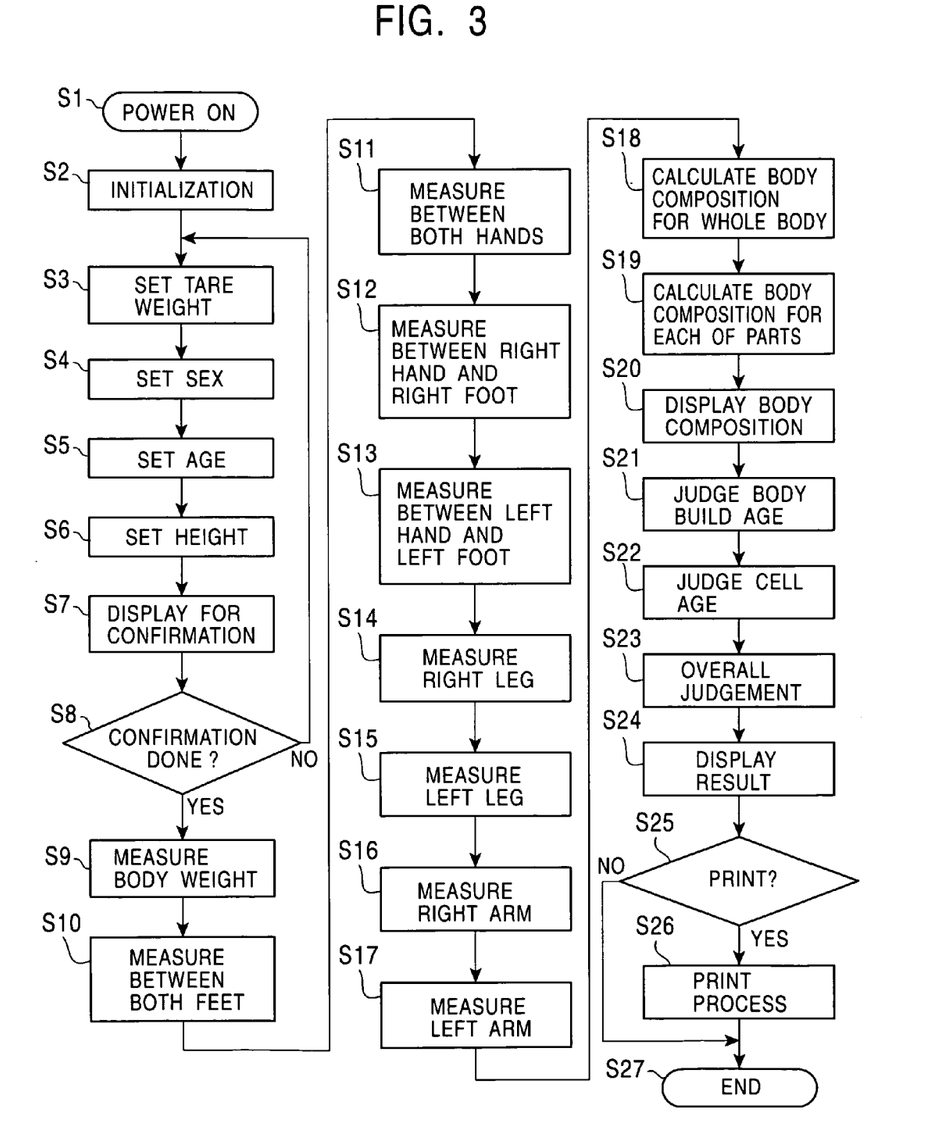
FIG. 3 is a flow chart illustrating an operation of the body composition measurement apparatus.

FIG. 3 is a flow chart illustrating an operation of the body composition measurement apparatus 1.

The power switch in the input unit 6 is depressed (step S1) to initialize the measurement apparatus (step S2). In personal parameter input mode the tare weight of a person under test is initially entered (step S3). Then, the personal parameters such as sex, age, height, etc. are entered using the numerical keys in the input unit 6 (steps S4 to S6).

The personal parameters entered are displayed on the display unit 7 for confirmation, together with a message for prompting the person to determine whether they are correct or not (step S7). If they are correct (step S8), the routine proceeds to a measurement process. But, if they are not correct the routine returns to step S3 in which the tare weight is entered, and the personal parameters are entered again.

After the personal parameters have been entered then the body weight of the person is measured (step S9). When the person mounts on the weight meter 2 the body weight of the person is detected and measured by the weight measurement unit 26.

Then, measurement of bioelectrical impedance of the person is performed using an electric current having a plurality of frequencies for each of the measured parts of the person's body.

Now, reference is made to a method for measurement of bioelectrical impedance. According to multi-frequency bioelectrical impedance measurement used herein not only the bioelectrical impedance but also the amount of body water, the amount of intracellular and extracellular water in a whole body, or alternatively the amount of water, the amount of intracellular and extracellular water in a measured part of the body can be derived on the basis of various types of living body parameters, intracellular water resistance, extracellular water resistance, cell membrane capacity, etc.

Figure 4:
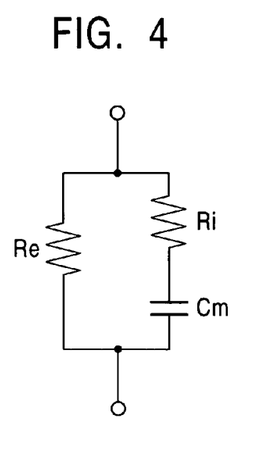
FIG. 4 is an electrical equivalent circuit for cells in a human body on the basis of which the present invention operates.

The bioelectrical impedance is normally represented by an equivalent circuit having concentrated constants consisting of extracellular water resistance "Re", intracellular water resistance "Ri" and cell membrane capacity "Cm", as shown in FIG. 4. Actually, the individual cells forming a living body are represented by the circuits each having different constant depending on the difference in geometry or characteristic thereof. Therefore, the living body made up of collection of those cells does not produce an impedance vector locus of half-circle as in the case of measurement of the equivalent circuit having concentrated constants, but produces a locus of an arc according to "Cole-Cole model".

Figure 5:
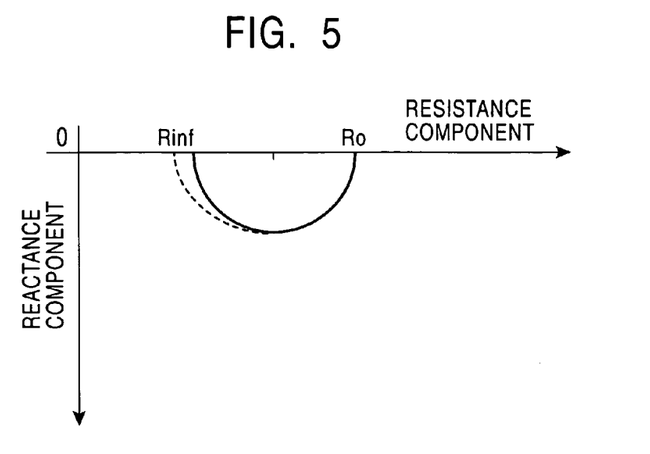
FIG. 5 is a view illustrating a vector locus of bioelectrical impedance for a human body for explanation of bioelectrical impedance measurement used in the present invention.

As the result, the bioelectrical impedance generally provides a locus of arc, as shown in FIG. 5. In this connection, the horizontal axis shows resistance component of the electrical impedance and the vertical axis shows reactance component thereof. Because of capacitance, the reactance component of bioelectrical impedance provides negative value so that the locus of the vector is present under the real axis, as shown in FIG. 5.

Figure 6:
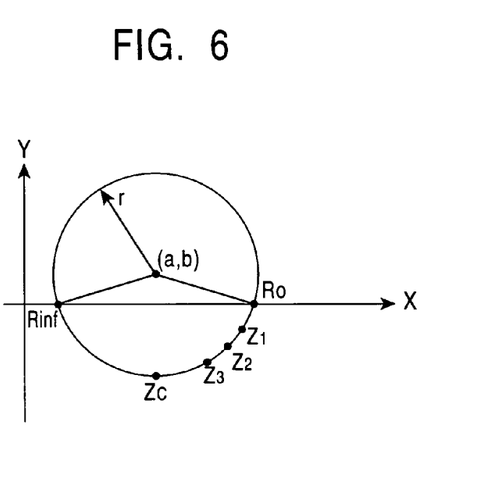
FIG. 6 is a graph illustrating the relation between 0 Hz frequency, "∞" frequency and characteristic frequency.

Referring to FIG. 6, the bioelectrical impedance values at frequencies 0 Hz, ∞ and Fc are represented by "Ro", "Rinf" and "Zc", respectively. The bioelectrical impedance values "Ro" and "Rinf" each has only resistance component because of reactance value of zero. The frequency Fc is one at which the absolute value of reactance component reaches the maximum, and "Zc" is the bioelectrical impedance at that frequency. It is assumed, here, that the frequency at which the absolute value of reactance component reaches the maximum is called "Characteristic Frequency". From those values or those approximated values the body composition such as the amount of body water, the amount of intracellular water, the amount of extracellular water, the fat free mass, the ratio of intracellular/extracellular water, etc. is calculated.

Now, measurement of bioelectrical impedance using AC current at multiple frequencies will be described in more detail.

The multi-frequency bioelectrical impedance measurement is repeated by "n" times that is preset, beginning with the frequency Fi=1. In initial setting for measurement at first frequency the setting of "i=1" is performed. The frequency "Fi" is set by the value of "i". On the basis of measurement control parameters already stored in ROM within the storage unit 24 the arithmetic controller unit 23 sets the frequency of output signal which is sent to the current source 21. The current source 21 includes a constant current output circuit in which the output current value can be set depending on the measurement control parameters. The AC output current is supplied to the person under test via the electrode switch unit 20 and the current supplying electrodes 3a, 4a, 13a, 14a.

Then, the current flowing through the person under test is detected by a reference resistor separately provided (not shown) of which analog output signal is converted into digital signal by an A/D converter within the arithmetic controller unit 23, which digital signal is then stored in RAM of the arithmetic controller unit 23. At the same time, the voltage is picked up by the voltage measurement electrodes 3b, 4b, 13b, 14b that are contact with the person under test, and then, it is sent to a differential amplifier within the voltage measurement unit 22. The differential amplifier produces a signal showing difference between the voltage signals sent thereto, which signal is then sent to the A/D converter within the arithmetic controller unit 23. The A/D converter converts analog input signal into digital signal, thereby measuring the bioelectrical impedance, which is then stored in RAM.

After the measurement of bioelectrical impedance at first frequency has been done setting of "i=i+1" is performed and a check is made to determine whether the measurement has been repeated by the predetermined number of times. If "i" is exceeded the predetermined number of times "n" then the measurement of bioelectrical impedance is terminated. But, if not exceeded, the measurement of bioelectrical impedance at the next frequency is performed.

Then, the impedance vector locus and the parameters associated therewith are calculated, based on the measurement values. Due to the reason, as described above, the bioelectrical impedance does not provide the impedance vector locus of a half-circle, but provides the vector locus of an arc according to "Cole-Cole model". As the result, the bioelectrical impedance generally provides the locus of arc, as shown in FIG. 5. From the assumption that the vector locus of arc is desired the bioelectrical impedance measurement values $Z_1, Z_2, \ldots Z_n$ at the frequencies "Fi" (i=1~n) are obtained, as plotted in FIG. 6. In this case, the real axis (or the horizontal axis) of the impedance plane is defined as "X" axis and the imaginary axis (or the vertical axis) is defined as "Y" axis.

From "Zi" (i=1~n) as plotted on the coordinate, the following correlation function is derived.

$$(X-a)^2+(Y-b)^2=r^2$$

where "a" is "X" coordinate at the center of a circle; "b" is "Y" coordinate at the center of the circle; and "r" is radius of the circle. Thus, the equation is an approximated correlation function among "n" points. Accordingly, the following equation is derived.

$$X=a\pm\sqrt{(r^2-b^2)}$$

Furthermore, because of Ro>Rinf, they are written as follows:

$$Ro=a+\sqrt{(r^2-b^2)}$$

$$Rinf=a-\sqrt{(r^2-b^2)}$$

Therefore, "Re" and "Ri" in the equivalent circuit in FIG. 4 are written as follows:

$$Re=Ro$$

$$Ri=Ro\cdot Rinf/(Ro-Rinf)$$

The impedance vector "Zc" at the characteristic frequency "Fc" is at such point that the absolute value of reactance, i.e., imaginary axis component or "Y" axis component reaches the maximum. Accordingly, "X" coordinate of the real axis component and "Y" coordinate of the imaginary axis component are written as follows:

$$X=a, Y=b-r$$

In other words, it may be written as follows:

$$Zc=a+j(b-r)$$

Thereby, the resistance component "R" and the reactance component "X" can be derived.

Depending on the derived impedance vector locus and the associated parameters such as "Ro" and "Rinf" or "Re" and "Ri" as well as the entered personal parameters such as sex, height, body weight, age, the amount of intracellular water "ICW", the amount of extracellular water "ECW", the ratio of intracellular/extracellular water "ICW/ECW", the amount of body water "TBW" (=ICW+ECW), etc. can be derived according to the well known calculation method. For example, the amount of intracellular water "ICW", the amount of extracellular water "ECW", and the amount of body water "TBW" are derived by the following equations using "Ri", "Re", height "Ht" and body weight "W".

$$ICW=K_{i1}Ht^2/Ri+K_{i2}W+K_{i3}$$

$$ECW=K_{e1}Ht^2/Re+K_{e2}W+K_{e3}$$

$$TBW=ICW+ECW$$

(where $K_{i1}, K_{i2}, K_{i3}, K_{e1}, K_{e2}, K_{e3}$ are coefficients.)

Returning to the flow chart of FIG. 3, description of operation of the apparatus is resumed. At first, measurement of the bioelectrical impedance between both feet of the person under test is performed (step S10). The electrode switch unit 20 is switched by the signal from the arithmetic controller unit 23 so that the current source 21 supplies AC current to the person under test via the electrodes 3a, 4a and the voltage across the electrodes 3b, 4b is measured by the voltage measurement unit 22. In this connection, as described above, measurement of bioelectrical impedance is performed at multiple frequencies to derive the resistance "R", reactance "X" and impedance "Z" between such parts of the person.

In the same manner, measurement of the bioelectrical impedance between both hands of the person is performed by flowing AC current to the person via the current supplying electrodes 13a, 14a and measuring voltage across the voltage measurement electrodes 13b, 14b (step S11).

Then, measurement of the bioelectrical impedance between a right hand and a right foot of the person is performed by flowing AC current to the person via the current supplying electrodes 14a, 4a and measuring voltage across the voltage measurement electrodes 14b, 4b (step S12).

Next, measurement of the bioelectrical impedance between a left hand and a left foot of the person is performed by flowing AC current to the person via the current supplying electrodes 13a, 3a and measuring voltage across the voltage measurement electrodes 13b, 3b (step S13).

Thereafter, measurement of the bioelectrical impedance for a right leg of the person is performed by flowing AC current to the person via the current supplying electrodes 14a, 4a and measuring voltage across the voltage measurement electrodes 3b, 4b (step S14).

Furthermore, measurement of the bioelectrical impedance for a left leg of the person is performed by flowing AC current to the person via the current supplying electrodes 13a, 3a and measuring voltage across the voltage measurement electrodes 3b, 4b (step S15).

Then, measurement of the bioelectrical impedance for a right arm of the person is performed by flowing AC current to the person via the current supplying electrodes 14a, 4a and measuring voltage across the voltage measurement electrodes 13b, 14b (step S16).

Then, measurement of the bioelectrical impedance for a left arm of the person is performed by flowing AC current to the person via the current supplying electrodes 13a, 3a and measuring voltage across the voltage measurement electrodes 13b, 14b (step S17).

After measurement of the bioelectrical impedance for each of the parts has been done the calculation of body composition for the person under test is performed. At first, the calculation of body composition for a whole body is performed (step S18).

The method of deriving the body fat rate, body fat mass and fat free mass for a whole body using the bioelectrical impedance will briefly be described, here, because it is well known in the art.

The body fat rate "% Fat", body fat mass "BFM" and fat free mass "FFM" are calculated using the body density "BD" in the manner as follows $$\% \text{ Fat} = (4.95/BD - 4.5) \times 100$$

$$BD = a - b \times W \times Z/H^2$$

$$BFM = W \times \% \text{ Fat}/100$$

$$FFM = W \times (1 - \% \text{ Fat})/100$$

where "W" (kg) is body weight; "H" (cm) is height; "Z" (Ω) is measured impedance; and "a", "b" are coefficients.

Thus, the body fat rate, body fat mass and fat free mass for a whole body are calculated using those equations.

Furthermore, depending on the bioelectrical impedance measured for each of the parts, the body weight measured and the height data entered, the body fat rate and fat free mass for each of four limbs can be calculated by comparison with the data obtained by "DEXA" measurement (Double X-ray Absorption Method). In addition, from the ratio of body fat rate to fat free mass, the weight of that part can be calculated, together with the body fat rate (step SC).

Moreover, the body fat mass, fat free mass and body fat rate for a trunk can be calculated by subtracting the body fat mass and fat free mass measured for each of the parts from those for a whole body.

Figure 7:
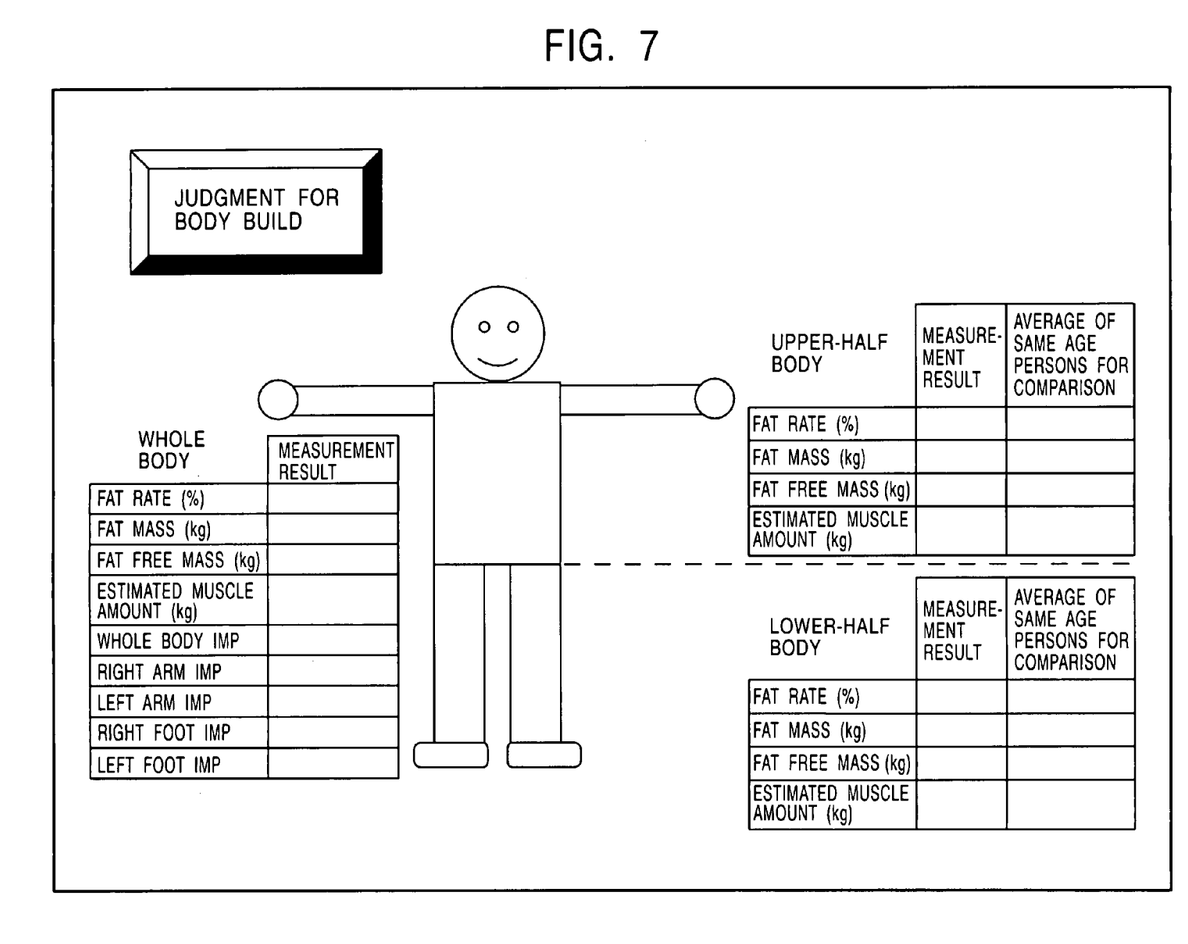
FIG. 7 is an example of display produced on the body composition measurement apparatus.

The results of calculation for a whole body and each of the parts are displayed, as shown in FIG. 7 (step SD). In particular, in FIG. 7, the body composition data is displayed for a whole body, an upper-half body and a lower-half body.

Figure 8:
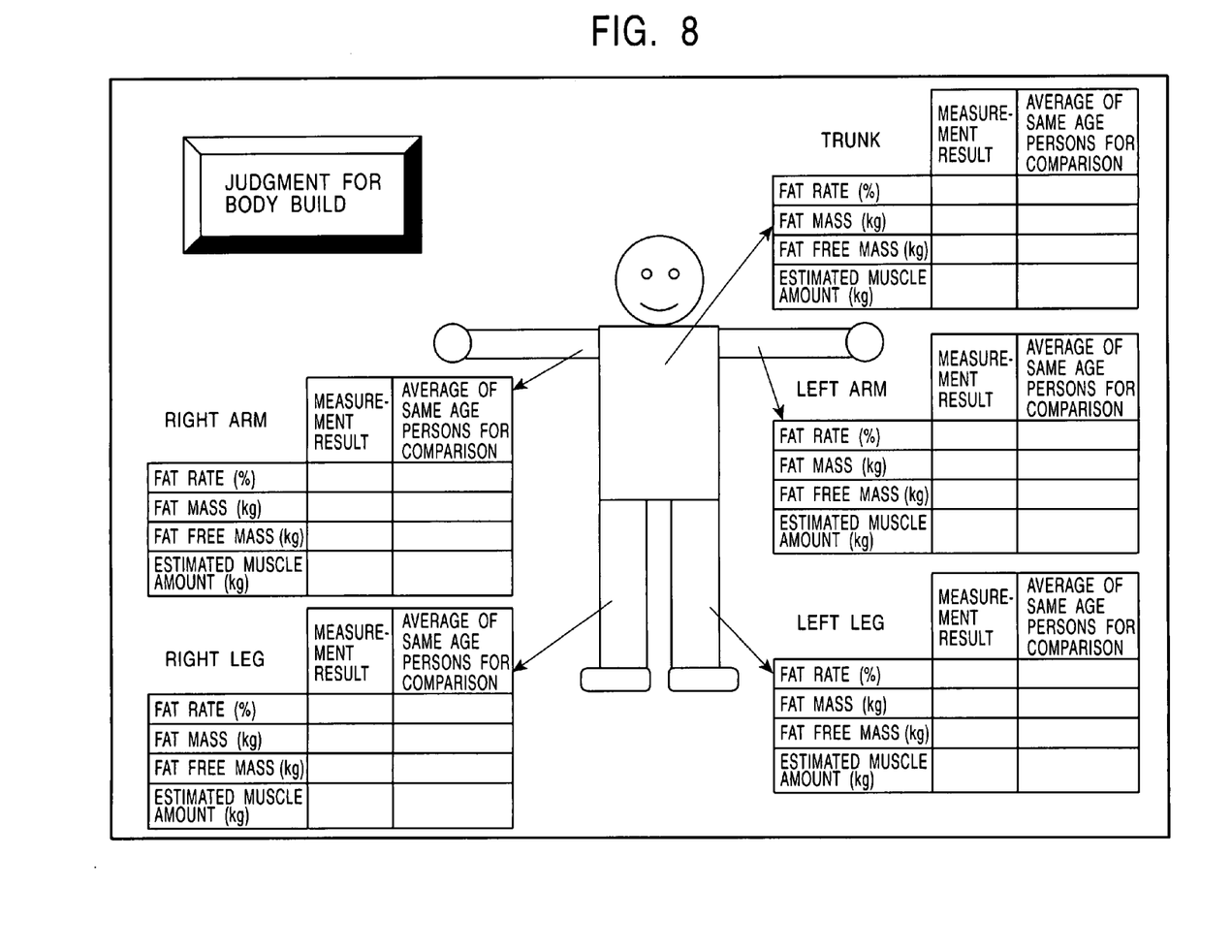
FIG. 8 is another example of display produced on the body composition measurement apparatus.

After a fixed time period has elapsed the display is switched to different one in which the body composition is displayed for each of the parts, as shown in FIG. 8. In particular, the body composition is displayed for each of 5 parts: trunk; right arm; left arm; right foot; and left foot.

The average value for the body composition of persons at the same age as the person under test is also displayed for the purpose of comparison, in addition to the body composition measured for each of the parts.

Then, decision is made to determine an index of person's body build age (step SC).

As described above, with the age, both male and female persons tend to increase fat especially on the upper arms and the trunks, but to reduce fat and muscle on the legs.

The index for fat only for the trunk or for combination of the trunk and upper arm becomes higher with the age, but the index for fat and muscle for the leg becomes lower with the age.

The index is determined, here, by a fraction of which numerator includes "trunk fat mass", "trunk fat rate", "trunk fat distribution rate", or each of them plus "upper arm fat mass", "upper arm fat rate", "upper arm fat distribution rate", and of which denominator includes "leg fat mass", "leg muscle amount", "leg muscle amount/body weight", "leg fat rate", "leg muscle rate", etc. Accordingly, the resulting value is proportion to the age.

In particular, the trunk fat distribution rate is one that is calculated according to the following equation:

$$\text{Trunk fat distribution rate} = (\text{trunk fat mass}/\text{whole body fat mass}) \times 100$$

The resulting value represents the rate of trunk fat mass relative to whole body fat mass. As described above, as the age is advanced the trunk body fat mass tends to increase, and therefore, smaller is the value, younger is the body build.

The index of body build age used in the embodiment is determined by the following equation using parameters that are considered most likely to produce any change with the age.

$$\text{Body Build Age} = a_1 \times (\text{trunk fat mass} + \text{upper arm fat mass})/(\text{leg muscle amount}) + c_1; \text{ or}$$

$$\text{Body Build Age} = a_2 \times (\text{trunk fat mass} + \text{upper arm fat mass})/(\text{leg muscle amount}/\text{body weight}) + c_2$$

(where "$a_n$", "$c_n$" are coefficient.)

The calculated "body build age" is used to derive the rate of difference from the real age that has been set at step S5.

$$\text{Rate of Difference from Real Age (\%)} = (\text{body build age} - \text{real age})/\text{real age} \times 100$$

Depending on the resulting value, body build age level is calculated as assessment for the body build in view of the age. The flowing three levels are provided according to the rate of difference from real age (%):

Less than −10%: Level 1=Body build younger than real age

−10%~+10%: Level 2=Body build equivalent to real age

Not less than +10%: Level 3=Body build older than real age

Figure 9:
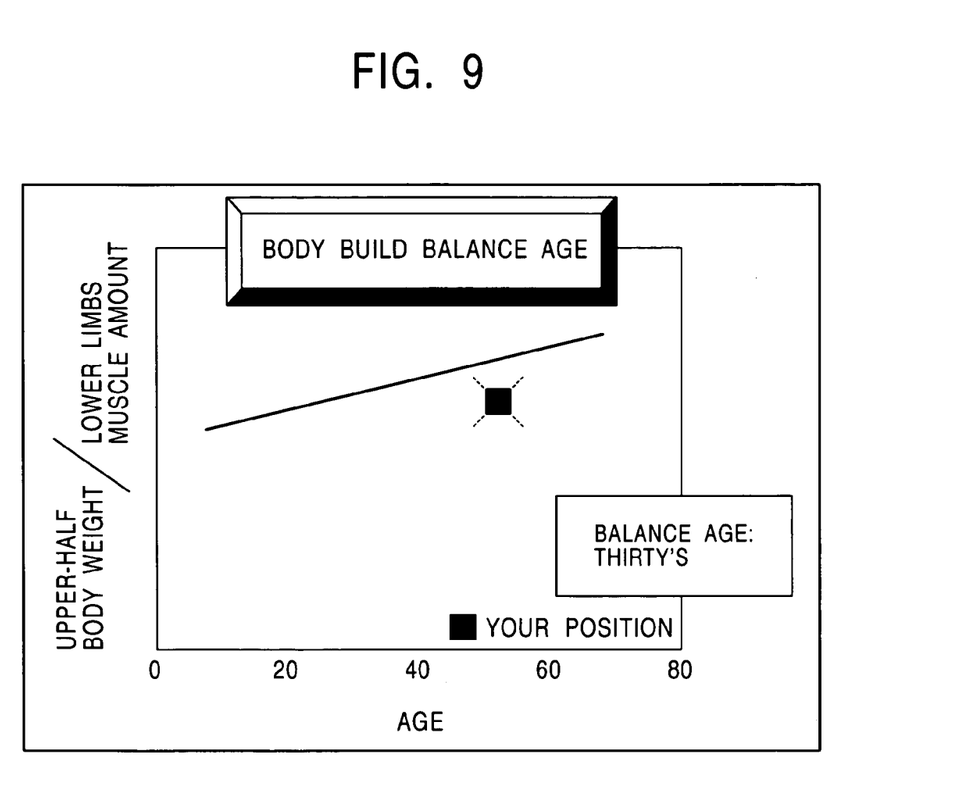
FIG. 9 is further example of display produced on the body composition measurement apparatus.

Then, the result of body build balance age is graphically displayed on the display unit 7, as shown in FIG. 9. This is the body build age that is calculated by "weight of an upper-half body/muscle amount in lower limbs". An average line representing the average value for each of the ages is also displayed in the graph.

Figure 10:
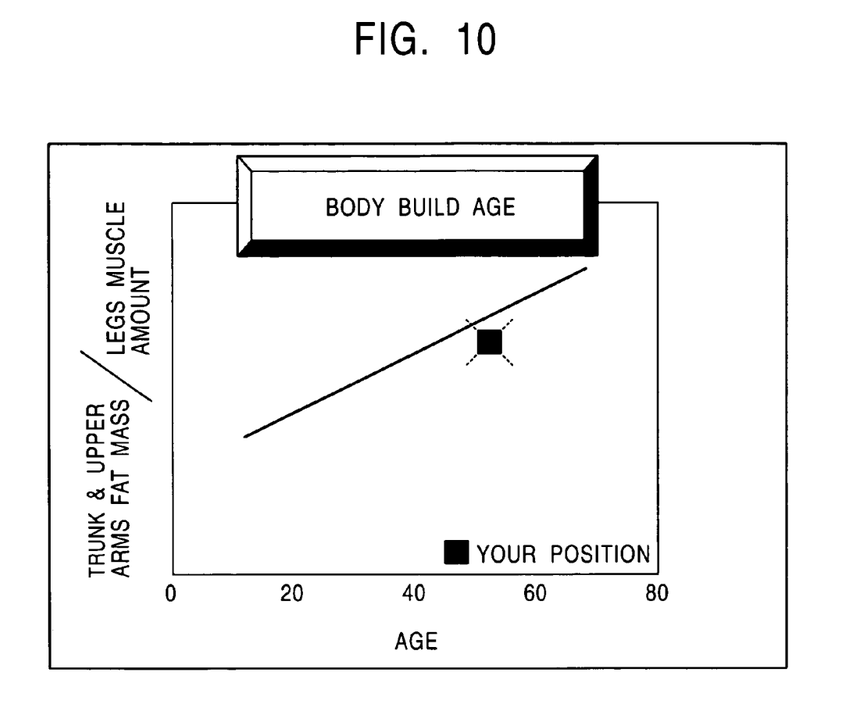
FIG. 10 is yet further example of display produced on the body composition measurement apparatus.

After a fixed time period has elapsed the result of body build age is graphically displayed, as shown in FIG. 10. This is calculated by "(trunk fat mass+upper arm fat mass)/(leg muscle amount)" as described above. In addition, an average line according to the age is displayed, whereby the person under test can understand how about he/she is as compared to the average for the same age.

Then, the index of cell age is calculated (step SD).

In general, there is tendency that the size of a cell (BCM) is reduced with the age. Accordingly, the ratio of intracellular water/extracellular water ($\approx Ri/Re$), the absolute value of reactance (Xc) reflecting the characteristic of cell membrane, the ratio of absolute value of reactance (Xc)/resistance (R), etc. are also reduced. In the present invention, any one of the following equations is used to calculate the cell age to determine the degree of aging at cell level ("$a_n$", "$b_n$" are coefficient).

(1) Size of a cell: in case where "BCM" is used:

$$\text{Cell Age} = a_1 \times \text{"BCM"} + b_1$$

(2) In case where the intracellular water amount "ICW" and extracellular water amount "ECW" are used:

$$\text{Cell Age} = a_2 \times \text{"ICW"}/\text{"ECW"} + b_2$$

(3) In case where the intracellular water resistance "Ri" and extracellular water resistance "Re" are used:

Cell Age=$a_3 \times$"Ri"/"Re"+$b_3$ (4) In case where two measurement frequencies "R1", "R2" are used ("R1"<"R2"):

Cell Age=$a_4 \times$"R1"/"R2"+$b_4$ (5) In case where the reactance "Xc" is used:

Cell Age=$a_5 \times |$"Xc"$|+b_5$ (6) In case where the reactance "Xc" and resistance "R" are used:

Cell Age=$a_6 \times |$"Xc"$|/$"R"+$b_6$

In the above equations the value calculated by the equation (1) is an index for simply showing the size of a cell; the value calculated by the equation (2) or (3) is an index on the basis of cell retained water; and the value calculated by any of other equations also represents the cell condition.

In this embodiment the cell age is calculated by the equation (1) using the size of a cell "BCM". In this respect, the size of a cell "BCM" is calculated as follows:

$BCM = a(bH^c/Xc^d) + eW - f$ where "H" (cm) is height, "W" (kg) is body weight, "Xc" (Ω) is reactance, and "a", "b", "c", "d", "e", "f" are coefficient.

Figure 11:
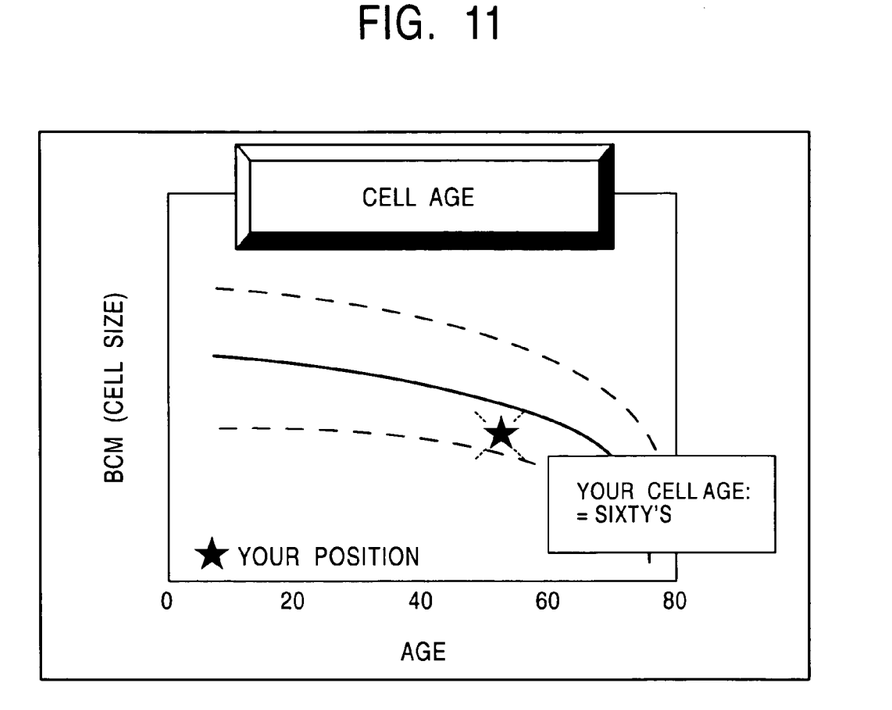
FIG. 11 is yet further example of display produced on the body composition measurement apparatus.

The "BCM" calculated and the cell age calculated using this "BCM" are displayed on the display unit 7, as shown in FIG. 11.

The calculated "cell age" is used to derive the rate of difference from the real age that has been set at step S5.

Rate of Difference from Real Age (%)=(cell age−real age)/real age×100

Depending on the resulting value, cell age level is calculated as assessment for the cell in view of the age. The flowing three levels are provided according to the rate of difference from real age (%):

Less than −10%: Level 1=Cell younger than real age
−10%~+10%: Level 2=Cell equivalent to real age
Not less than +10%: Level 3=Cell older than real age Then, depending on the result of body build age and cell age the total assessment for the body composition of the person under test is performed (step S23). This is for the purpose of displaying the result of assessment and an advice message on the basis of combination of the body build age and cell age, as shown in FIG. 12.

Figure 13:
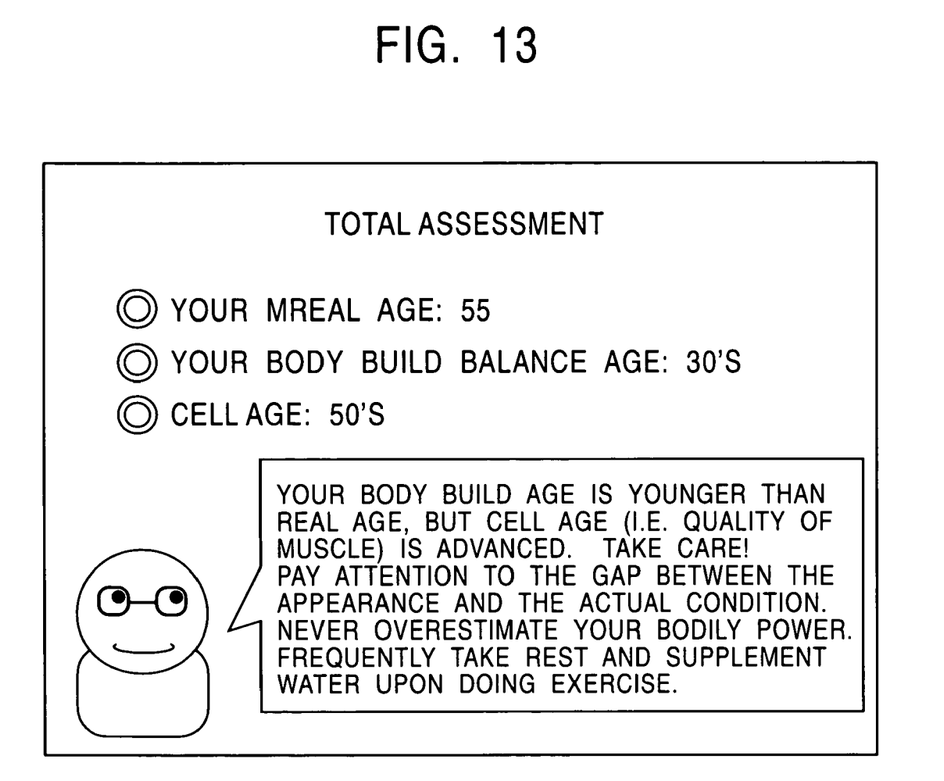
FIG. 13 is yet further example of display produced on the body composition measurement apparatus.

FIG. 13 shows a display of total assessment as selected from the table of FIG. 12 (step S24).

If the print switch on the input unit 6 is depressed the printer unit 8 prints the measurement result on a paper which is then discharged (step S25, S26).

However, if the print switch is not depressed at step S25 the power supply is turned OFF after a fixed time period to terminate all the operation of the apparatus (step S27).

As described above, in one embodiment of the present invention, the multi-frequency bioelectrical impedance measurement has been performed to derive the resistance and reactance components that are used for the index of body build age and cell age. Alternatively, a single-frequency bioelectrical impedance measurement may be performed to derive the resistance and reactance components that are used for the index of body build age and cell age.

In the above embodiment the index of cell age or body build age has been described as showing a whole body cell age or body build age. Alternatively, another embodiment may be considered in which the average value for muscle amount, fat mass or "BCM" for each of the parts of the person at each of the ages is stored and the measurement data for each of the parts is compared to that average value to produce the cell age or body build age for each of the parts.

Furthermore, in addition to the index of height, body weight or bioelectrical impedance used in assessment for body build in the above embodiment, an additional parameter such as the waist size, the size of clothes, or the size of underwear especially for woman may be used to provide more precise assessment for the body build.

It is apparent from the foregoing that a body composition measurement apparatus of the present invention allows judgment for any change in the index reflecting the cells of a person under test with the age. Therefore, internal assessment for cells of the person's body, which can't externally be seen, can be performed in order to provide more useful assessment for the body composition of the person under test in view of the quality of muscle.

Furthermore, the body composition measurement apparatus of the present invention allows judgment for youngness of the person under test in view of his/her body build depending on the balance of distribution of trunk fat and whole body fat as well as the balance of parts including fat and muscle. Therefore, it is possible to advantageously determine what age the body build of the person belongs to.

In addition, the body composition measurement apparatus of the present invention allows judgment for the body composition of the person under test with combination of two types of comparison: one is comparison of any change in cell with the age to the real age of the person; and the other is comparison of any change in body build with the age to the real age of the person. Accordingly, the body composition of the person under test can be assessed at both internal and external sides to provide precise and useful assessment for the body composition.

Moreover, the body composition measurement apparatus of the present invention can produce any suitable advice message depending on the result of assessment of body composition by taking into account of main body fat that is intimately related to dangerous factor for lifestyle related disease, which can advantageously assist for prevention of any lifestyle related disease.

What is claimed is:

1. A body composition measurement apparatus, comprising:
    a current supplying unit;
    a voltage measurement unit;
    a bioelectrical impedance measurement unit; and
    a judgment unit, wherein
    said current supplying unit supplies an electric current to a person under test,
    said voltage measurement unit measures an electric voltage,
    said bioelectrical impedance measurement unit measures a parameter for bioelectrical impedance of a measured part of the person, based on the current supplied and the voltage measured, and
    said judgment unit judges an index for cell age of the person, based on the measured parameter for bioelectrical impedance.

2. A body composition measurement apparatus according to claim 1 in which size of a cell is used as the index for cell age.

3. A body composition measurement apparatus according to claim 1 in which cell-retained water is used as the index for cell age.

4. A body composition measurement apparatus according to any one of claims 1 to 3 in which said judgment unit compares the judged index for cell age to the real age of the person for assessing the cell age of the person.

5. The apparatus of claim 1, wherein the judgment unit calculates the cell age using the following formula:

Cell Age=$a_1 \times BCM + b_1$ where $a_1$ and $b_1$ are coefficients, and

BCM=$a(bH^c/Xc^d)+eW-f$, where H is a height of the person under test, W is a body weight of the person under test, Xc is a reactance component of the bioelectrical impedance, and a, b, c, d, e, and f are coefficients.

6. The apparatus of claim 1, wherein the judgment unit calculates the cell age using the following formula:

Cell Age=$a_2 \times ICW/ECW + b_2$ where $a_2$ and $b_2$ are coefficients, ICW is an intracellular water amount, and ECW is an extracellular water amount, wherein the judgment unit is for calculating ICW and ECW based on the bioelectrical impedance.

7. The apparatus of claim 1, wherein the judgment unit calculates the cell age using the following formula:

Cell Age=$a_3 \times Ri/Re + b_3$ where $a_3$ and $b_3$ are coefficients, Ri is an intracellular water resistance, and Re is an extracellular water resistance, wherein the judgment unit is for calculating Ri and Re based on the bioelectrical impedance.

8. The apparatus of claim 1, wherein the current supplying unit supplies the electric current at a plurality of frequencies R1 and R2, wherein R1<R2, and wherein the judgment unit calculates the cell age using the following formula:

Cell Age=$a_4 \times R1/R2 b_4$ where $a_4$ and $b_4$ are coefficients.

9. The apparatus of claim 1, wherein the judgment unit calculates the cell age using the following formula:

Cell Age=$a_5 \times |Xc| + b_5$ where $a_5$ and $b_5$ are coefficients, and Xc is a reactance component of the bioelectrical impedance.

10. The apparatus of claim 1, wherein the judgment unit calculates the cell age using the following formula:

Cell Age=$a_6 \times |Xc|/R + b_6$ where $a_6$ and $b_6$ are coefficients, Xc is a reactance component of the bioelectrical impedance, and R is a resistance component of the bioelectrical impedance.

11. A body composition measurement apparatus, comprising:
a current supplying unit;
a voltage measurement unit;
a bioelectrical impedance measurement unit; and
a judgment unit, wherein
said current supplying unit supplies an electric current to a person under test,
said voltage measurement unit measures an electric voltage,
said bioelectrical impedance measurement unit measures a parameter for bioelectrical impedance of a measured part of the person, based on the current supplied and the voltage measured, and
said judgment unit judges an index for body build age of the person, based on the measured parameter for bioelectrical impedance.

12. A body composition measurement apparatus according to claim 11 in which said index for body build age has such value that is calculated based on a parameter for main body fat and a parameter for leg fat or muscle.

13. A body composition measurement apparatus according to claim 11 in which main body fat distribution rate is used as the index for body build age.

14. A body composition measurement apparatus according to any one of claims 11 to 13 in which said judgment unit compares said judged index for body build age to the real age of the person for assessing the body build age of the person.

15. The apparatus of claim 11, wherein the measured part of the person comprises the trunk, an upper arm and a leg,
wherein the judgment unit calculates a trunk fat mass, an upper arm fat mass, and a leg muscle amount based on the bioelectrical impedance, and
wherein the judgment unit calculates the body build age using the following formula:

Body Build Age=$a_7 \times$(trunk fat mass+upper arm fat mass)/(leg muscle amount)+$c_7$ where $a_7$ and $c_7$ are coefficients.

16. The apparatus of claim 11, wherein the measured part of the person comprises the trunk, an upper arm and a leg,
wherein the judgment unit calculates a trunk fat mass, an upper arm fat mass, and a leg muscle amount based on the bioelectrical impedance, and
wherein the judgment unit calculates the body build age using the following formula:

Body Build Age=$a_8 \times$(trunk fat mass+upper arm fat mass)/(leg muscle amount/body weight)+$c_8$ where $a_8$ and $c_8$ are coefficients.

17. A body composition measurement apparatus, comprising:
a current supplying unit;
a voltage measurement unit;
a bioelectrical impedance measurement unit; and
a judgment unit, wherein
said current supplying unit supplies an electric current to a person under test,
said voltage measurement unit measures an electric voltage,
said bioelectrical impedance measurement unit measures a parameter for bioelectrical impedance of a measured part of the person, based on the current supplied and the voltage measured, and
said judgment unit includes
an index change judgment portion that judges any change in index for cell and body of the person with the age, based on the measured parameter for bioelectrical impedance,
a cell assessment portion that compares the judged change in index for cell with the age to the real age of the person for assessing the cell age of the person, and
a body build assessment portion that compares the judged change in index for body build with the age to the real age of the person for assessing the body build of the person, whereby the body composition of the person in view of the age is judged, based on the combination of said assessments for the cell age and the body build age of the person.

18. A body composition measurement apparatus according to claim 17 in which it further comprises an advice generation unit, said advice generation unit generating an advice message in response to the judged body composition of the person in view of the age.

* * * * *